(12) United States Patent
Shakespeare et al.

(10) Patent No.: US 6,272,440 B1
(45) Date of Patent: Aug. 7, 2001

(54) METHOD AND APPARATUS FOR MEASURING COLOR AND/OR COMPOSITION

(75) Inventors: John Shakespeare; Tarja Shakespeare, both of Siuro (FI)

(73) Assignee: Metso Paper Automation, Inc., Tampere (FI)

(*) Notice: Subject to any disclaimer, the term of this patent is extended or adjusted under 35 U.S.C. 154(b) by 0 days.

(21) Appl. No.: 09/205,671

(22) Filed: Dec. 4, 1998

Related U.S. Application Data

(60) Provisional application No. 60/069,275, filed on Dec. 11, 1997.

(51) Int. Cl.[7] .................................................. G01N 21/27
(52) U.S. Cl. .............................. 702/85; 356/73; 356/407; 356/408; 356/425; 250/559.04
(58) Field of Search ........................ 702/85; 250/559.04, 250/226; 356/73, 418–419, 408, 425, 402, 407

(56) References Cited

U.S. PATENT DOCUMENTS

| 4,439,038 | * | 3/1984 | Mactaggart | 356/408 |
| 4,565,444 | * | 1/1986 | Mactaggart | 356/73 |
| 4,801,809 | * | 1/1989 | Burk et al. | 250/559.04 |

FOREIGN PATENT DOCUMENTS 2098725   11/1982 (GB).

* cited by examiner

Primary Examiner—Marc S. Hoff
Assistant Examiner—Hien Vo
(74) Attorney, Agent, or Firm—Ladas & Parry

(57) ABSTRACT

The invention relates to a method and apparatus for determining the color and/or composition of a material. A sample of the material is illuminated with at least three separate illumination bands singly or in combination, said illumination bands collectively substantially spanning at least the visible range. The light reflected or transmitted by the sample is measured with at least four light detector elements responsive to light in wavelength bands which substantially span the visible range when the sample is illuminated. The width of the illumination bands differs in such a manner that the illumination bands are narrowest near the expected fluorescence absorption bands.

39 Claims, 1 Drawing Sheet

METHOD AND APPARATUS FOR MEASURING COLOR AND/OR COMPOSITION

Figure 1:
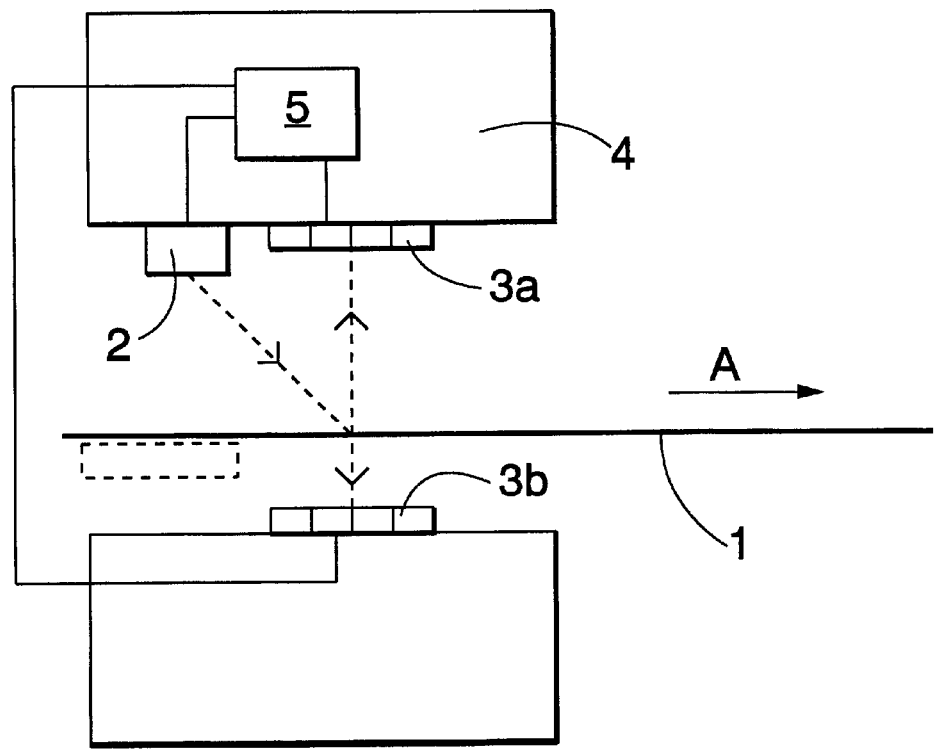

This application claims the benefit of U.S. Provisional Application (s) No(s).: Application No(s).: 60/069,275 filing date Dec. 11, 1997.

BACKGROUND OF THE INVENTION

The invention relates to a method for determining the color and/or composition of a material.

The invention further relates to an apparatus for determining color and/or composition of a material.

Color is a property of an object which depends on the object, conditions of illumination, and the observer. In general, the light reflected or transmitted by a non-self-luminous object depends on the nature of the light simultaneously incident on the object, and the geometrical relation of the light source and object. The perceived color of the reflected or transmitted light depends additionally on the visual receptivity of the observer, and the geometrical relation of the observer to said light.

The apparent reflectance of a non-self-luminous object in a particular geometrical relation to the light source and observer is defined to be the ratio of the spectral power in each wavelength band of the reflected light to the spectral power of the same wavelength band of the incident light:

$$R(\lambda) = \frac{reflected(\lambda)}{incident(\lambda)} \qquad (1)$$

Similarly, the apparent transmittance of a non-self-luminous object in a particular relation to the light source and observer is defined to be the ratio of the spectral power in each wavelength band of the transmitted light to the spectral power of the same wavelength band of the incident light:

$$T(\lambda) = \frac{transmitted(\lambda)}{incident(\lambda)} \qquad (2)$$

Absorbance is often used instead of transmittance, being the ratio of spectral power in each wavelength band of the absorbed light to the spectral power of the same wavelength band of the incident light. Thus, it is the complement of transmittance:

$$A(\lambda) = \frac{absorbed(\lambda)}{incident(\lambda)} = 1 - \frac{transmitted(\lambda)}{incident(\lambda)} = 1 - T(\lambda) \qquad (3)$$

An alternative definition of absorbance is the logarithm of the absorbance as defined in (3). Absorbance and transmittance are interchangeable by trivial modification of any expression in which one or the other appears. In this specification, where either absorbance or transmittance is used, it is to be understood in each case that the equivalent formulation using the other is tacitly implied and within the scope of the specification. Similarly, while this specification expresses reflectance, transmittance, and other quantities as functions of wavelengths, equivalent expressions as functions of frequency or wave number are also in common use. These quantities can be easily converted between the different formulations. Thus, wherever a quantity is expressed as a function of wavelength, it is to be understood in each case that the equivalent formulations using functions of frequency or wave number are tacitly implied and within the scope of the specification.

Clearly, reflectance and transmittance as defined in (1) and (2) have meaning only for wavelength bands in which the incident light has sufficient power to be detectable. Accordingly, rich light sources, having significant amounts of energy at all humanly visible wavelengths, are normally used for measuring them.

Since the perceived color of an object depends on so many factors, standardization of definitions is most important for each of the variables. Standards authorities, such as the CIE (Commission Internationale d'Éclairage), have specified generally accepted standard illuminants having particular spectral power distributions, and color measurement devices usually contain means for approximating one or two such illuminants. Such means is often a rich physical light source with specific optical filters. The C, D55, D65, and D75 sources are frequently encountered, but others such as A, D60, F2, etc. may also be found in industrial applications.

Similarly, since human observers may match color samples differently depending on the size of the color samples, standard spectral observers have been defined for 2 degree and 10 degree fields of view.

Since human vision reduces many wavelength bands in a light spectrum into a three dimensional signal in the retina, color is conventionally expressed as colorimetric quantities having three values. Colorimetric systems in common use include for example CIE Tristimulus; CIE Chromaticity, Lightness; CIE L*a*b*; Hunter L,a,b; Hue Angle, Saturation Value and Dominant wavelength, Excitation purity, Lightness.

Under given conditions of illumination and geometry, CIE tristimulus values may be calculated for the standard spectral observers using formulae which are defined by the CIE. These tristimulus values provide a base from which the other colorimetric quantities can be calculated using formulae defined by the pertinent standards authorities. Such formulae are occasionally revised, as the state of the art is improved. Some auxiliary colorimetric quantities are also of importance in appearance specifications. These are also derived from the tristimulus values, with definitions provided by the CIE and other standards authorities. They include for example tint; whiteness index; yellowness index and blue reflectance.

The tristimulus values are calculated from the apparent reflectance or transmittance of an object, using the spectral power distribution of the illuminant for which the object's color appearance is to be evaluated. Conventionally, tristimulus values are defined as integrals but are normally evaluated as finite approximations:

$$X = k \int_{380}^{780} R(\lambda)S(\lambda)\underline{x}(\lambda)\,d\lambda = k \sum_{j=1}^{N} R_j S_j \underline{x}_j \delta\lambda \qquad (4a)$$

$$Y = k \int_{380}^{780} R(\lambda)S(\lambda)\underline{y}(\lambda)\,d\lambda = k \sum_{j=1}^{N} R_j S_j \underline{y}_j \delta\lambda \qquad (4b)$$

$$Z = k \int_{380}^{780} R(\lambda)S(\lambda)\underline{z}(\lambda)\,d\lambda = k \sum_{j=1}^{N} R_j S_j \underline{z}_j \delta\lambda \qquad (4c)$$

where k is a normalization factor, S is the spectral power distribution of the target illuminant, and x, y, z, are the standard observer functions, tabulated at uniform wavelength intervals. In the case that the reflectance data is abridged or truncated, or measured at non-standard wavelength intervals, there are various recommended techniques for interpolation, extrapolation or resampling. Similar equations to (4a–4c) and corresponding methods are used in calculating tristimulus from transmittance spectra. Note that the spectral power distribution of the illuminant used in evaluations (4a–4c) need not be the same as the spectral power distribution of the source used to illuminate the sample during measurement of reflectance or transmittance. It is assumed that the reflectance and transmittance do not depend on the light source.

Each industry tends to have a preferred colorimetric system, although there may be regional differences in such preference. For example, Hunter L,a,b is used widely in the papermaking industry in the U.S.A., but rarely elsewhere, as CIE L*a*b is preferred in the papermaking industry in most other regions, and is also used in the U.S.A. The CIE L*a*b values are defined (1976) for photopic conditions as follows:

$$L^* = 116(Y/Y_n)^{1/3} - 16 \tag{5a}$$

$$a^* = 500[(X/X_n)^{1/3} - (Y/Y_n)^{1/3}] \tag{5b}$$

$$b^* = 200[(Y/Y_n)^{1/3} - (Z/Z_n)^{1/3}] \tag{5c}$$

where $X_n$, $Y_n$, and $Z_n$ are the tristimulus values for the illuminant. Photopic conditions exist when the ratios $X/X_n$, $Y/Y_n$, and $Z/Z_n$ all exceed 0.008856; otherwise either mesopic or scotopic conditions exist, and the equations used differ from (5a), (5b) and (5c), as described in ASTM test method E308-90, for example. These and other issues of colorimetry are well known per se, and are not further discussed. Measurement of color and evaluation of colorimetric quantities in photopic, mesopic, and scotopic conditions are contemplated by, and within the scope of the present invention.

Auxiliary non-colorimetric quantities are of importance in some industries. For example, indices of brightness may be derived from the reflectance spectrum, whereas indices of opacity and transparency may be derived from the transmittance spectrum. Definitions of these and other non-standardized quantities are often industry-specific. However, in their respective fields of application, they are of equal importance to the standardized colorimetric quantities.

The foregoing discussion pertains to describing the measured color of a sample. However, in the case that the sample is not opaque, it may be necessary to calculate the color which would be measured from a stack of samples which is thick enough to be effectively opaque. The transmittance of such a stack is obviously zero, so we are concerned only with its reflectance.

Often, a sufficient number of substantially identical samples can be stacked, and the measurement made directly thereon. However, in other cases this may not be practical—for instance, if the measurement is made on a moving sheet during manufacture. There are several multi-flux models which allow calculation of the infinite stack reflectance from measurements of sample reflectance and transmittance, and some knowledge of the relative absorbing and scattering power of the sample. One which is in widespread use in sheet forming industries is the Kubelka-Munk two-flux model, for diffuse light fluxes in both directions. Another is the four-flux model, which incorporates directional light fluxes in addition to the diffuse light fluxes.

If the quality specification for a translucent material is given in terms of the color of an infinite (or opaque) stack of samples, it is also necessary to perform the inverse calculations to derive a single-layer color from an infinite stack color. Similarly, these techniques can be used to calculate the color which would be measured from a sample of different thickness to the measured sample. In this case, the thickness need not be a multiple of the sample thickness, and may be less than or greater than the sample thickness. Since, in the general case, such calculation need not be for an opaque thickness, both reflectance and transmittance may be so calculated.

The equations and methods of multi-flux models, including the four-flux and Kubelka-Munk two-flux models may be found in Völz, H. G., "Industrial Color Testing", VCH, Weinheim Germany, 1995, among others. These models do not incorporate fluorescence or other spectral transformations; they only model absorption and scattering phenomena.

The difference in color between two samples, or between a sample and a color specification, can be evaluated on the basis of the available measurements. Customarily, a numerical expression of such a color difference is used to determine acceptability of manufactured items, by comparing that numerical value to the allowable maximum value. Depending on the number and type of color variables measured or specified, more than one method of evaluating color difference may be thus employed.

As an example, a commonly used expression for color difference in a colorimetric system is the distance between the co-ordinates of the compared measurements. The CIE L*a*b* color difference is defined (1976) as:

$$\Delta E^* = [(\Delta L^*)^2 + (\Delta a^*)^2 + (\Delta b^*)^2] \tag{6}$$

A refinement of (6) was promulgated in 1994, but is not yet in widespread use in industry. Analogous definitions exist for other colorimetric systems, and specialized methods for evaluating color difference exist in specific industries.

It is possible for two different reflectance or transmittance curves to produce identical tristimulus or other colorimetric quantities under specific conditions of the illuminant and observation. However, if the illuminant or observer is changed, the colorimetric quantities will no longer match. This phenomenon is known as metamerism.

To avoid source metamerism and field metamerism, the color specification for an object may be supplied in spectral form, as reflectance and/or transmittance curves. In the absence of fluorescence, reflectance curves are invariant with changes to the illuminant. Thus, if the reflectance and transmittance curves match for two samples under one illuminant, they will have matching tristimulus and other colorimetric values under all illuminants and observers.

Instrument metamerism is the phenomenon whereby one color measurement device may indicate that a pair of samples match in color, while another color measurement device indicates a color mismatch. Instrument metamerism arises in spectrophotometric devices through differences in source spectrum, polychromator characteristics, number and wavelength of photodetector elements, and internal standards, among others.

The color of a non-self-luminous opaque sample is commonly measured by means of spectrophotometers in which a sample is illuminated with a particular rich light source (one having significant energy at all visible wavelengths), usually filtered to approximate a standard illuminant, and the reflected light is measured at several wavelengths in the visible band. The sample may be continuously illuminated, using a constant light source, or intermittently, using a flashing source.

In the case of a non-self-luminous translucent sample, the transmitted light may be measured additionally or alternatively to the reflected light by means of a detector on the opposite side of the sample to the illuminant. In other prior art apparatuses, the transmitted light can be reflected back through the sample by a suitable reflector opposite the illuminant such that the detector for transmitted light is on the same side as the illuminant and the detector for reflected light. By suitable means for alternating a reflective white backing with a non-reflective black backing, a device may use a single detector to measure reflected light and reflected light with doubly transmitted light alternately. Estimates of the single layer transmittance and of the infinite stack reflectance may then be derived by suitable calculations. For example, if the black backing is completely non-reflective, then the following Kubelka-Munk equation (given in Wendtland, W. W. and Hecht, H. G., "Reflectance Spectroscopy", Wiley, New York USA, 1966) may be used to estimate the infinite stack reflectance:

$$R_\infty(\lambda) = \frac{R_{white}(\lambda)}{2} + \frac{R_{black}(\lambda) - R_{white}(\lambda) + R_{backing}(\lambda)}{2R_{black}(\lambda)R_{backing}(\lambda)} \quad (7)$$

where $R_{white}$ is the reflectance with white backing, $R_{black}$ is the reflectance with black backing, and $R_{backing}$ is the reflectance of the white backing.

In practice, the reflectance is rarely calculated using (1). Instead, the reflected light is compared to the reflected light obtained when a reference sample of known reflectance is placed in the sample location and illuminated with the same source:

$$R(\lambda) = \frac{reflect(\lambda)}{reflect_{ref}(\lambda)} R_{ref}(\lambda) \quad (8)$$

In all these cases of prior art, neither true reflectance nor true transmittance is measured. Rather, the measuring device measures the apparent reflectance and/or the apparent transmittance. This is a consequence of measuring all wavelength bands of the reflected or transmitted light while illuminating with a rich light source.

The apparent reflectance of an infinite stack is often calculated from the apparent reflectance of a single layer, and inverse calculations are often performed for apparent reflectance targets, as disclosed by U.S. Pat. No. 5,082,529. This adjustment typically uses methods based on the Kubelka-Munk two-flux model, even in cases where it is inappropriate (e.g. when the instrumental illumination contains a directional radiance, and is not purely diffuse).

Whereas the true reflectance and transmittance at each wavelength is at most unity, the apparent reflectance and apparent transmittance may exceed unity due to fluorescence. The process of fluorescence involves absorption of light in a range of wavelengths termed the absorption band, and the emission of part of that absorbed energy as light in an emission band, containing longer wavelengths than the absorption band, but which may partly overlap the absorption band. The efficiency of absorption may vary at different wavelengths in the absorption band. Each wavelength in the absorption band can have a different efficiency of emission at each of the wavelengths in the emission band. If the incident light contains sufficient power in the absorption band of a fluorescent object, the light consequently emitted in its emission band, when combined with light reflected or transmitted in the emission band, can yield an apparent reflectance or transmittance in the emission band which is greater than unity. If there is little or no incident light in the emission band, the apparent reflectance or transmittance in that band may be much greater than unity. Note that, regardless of whether the light absorbed in a fluorescent relation is directional or diffuse, the emitted light will generally be diffuse.

In this specification, we shall continue to use the terms "reflected" and "transmitted" to describe respectively the light excident from a sample on the same side as the illumination and on the opposite side, including the effects of fluorescent emission. Note that while the above mentioned multi-flux models incorporate absorption and scattering, they do not incorporate spectral transformations of the kind under discussion here.

These processes can be expressed in the following way:

$$reflected(\lambda) = \int_{min}^{780} E(\lambda, \zeta)S(\zeta)d\zeta \quad (9a)$$

$$transmitted(\lambda) = \int_{min}^{780} U(\lambda, \zeta)S(\zeta)d\zeta \quad (9b)$$

where $E(\lambda,\zeta)$ is the apparent emissivity of the sample, being the ratio of light apparently reflected at wavelength $\lambda$ to the light incident at wavelength $\zeta$, and $U(\lambda,\zeta)$ is the apparent transmissivity of the sample, being the ratio of light apparently transmitted at wavelength $\lambda$ to the light incident at wavelength $\zeta$. The lower limit of each integration, min, is a wavelength below the fluorescence absorption band of the sample; in practical cases, this wavelength is generally 200 nm or higher. Matrix representation of emissivity and transmissivity provide finite approximations:

$$reflected(\lambda_j) = \sum_{k=1}^{M} E_{jk} S_k \Delta\zeta_k \quad (10a)$$

$$transmitted(\lambda_j) = \sum_{k=1}^{M} U_{jk} S_k \Delta\zeta_k \quad (10b)$$

where $E_{jk}$ and $U_{jk}$ are respectively the apparent emissivity matrix and apparent transmissivity matrix, with elements defined for quantum relations between discrete wavelength bands, centered on specific sets of wavelengths $\lambda_j$, $\zeta_k$, and $\Delta\zeta_k$ is the width of the wavelength band centered on $\zeta_k$. For instance:

$$E_{jk} = \int_{\frac{\lambda_j+\lambda_{j-1}}{2}}^{\frac{\lambda_j+\lambda_{j+1}}{2}} \int_{\frac{\zeta_k+\zeta_{k-1}}{2}}^{\frac{\zeta_k+\zeta_{k+1}}{2}} E(\lambda, \zeta)d\zeta d\lambda \quad (11a)$$

$$j = 1...N,$$
$$k = 1...M$$

$$U_{jk} = \int_{\frac{\lambda_j+\lambda_{j-1}}{2}}^{\frac{\lambda_j+\lambda_{j+1}}{2}} \int_{\frac{\zeta_k+\zeta_{k-1}}{2}}^{\frac{\zeta_k+\zeta_{k+1}}{2}} U(\lambda, \zeta)d\zeta d\lambda \quad (11b)$$

$$j = 1...N,$$
$$k = 1...M$$

Thus, the light apparently reflected from a sample depends on the apparent emissivity matrix of the sample as well as on the light incident on the sample. In the same way, the light transmitted through a translucent sample depends on the apparent transmissivity of the sample as well as on the light incident on the sample.

For non-fluorescent samples, the apparent emissivity $E_{jk}$ is nonzero only for elements where $\lambda_j=\zeta_k$, and these emissivity values are the reflectance values at those wavelengths. Similarly, the apparent transmissivity $U_{jk}$ of a non-fluorescent translucent sample is nonzero only for elements where $\lambda_j = \zeta_k$, and these transmissivity values are the transmittance values at those wavelengths. For fluorescent samples the emissivity and, if translucent, the transmissivity have nonzero values for some elements where $\lambda_j > \zeta_k$.

It is clear from (9a) or (10a) combined with (1) or (8) that for a fluorescent sample, there can be a difference between its apparent reflectance curves measured under different conditions of illumination. The degree to which the apparent reflectance curves differ depends on the degree to which the illuminants differ in their spectral power distribution in the fluorescence absorption and emission bands. The apparent transmittance of a translucent fluorescent sample will depend in an analogous way on the spectral distribution of illuminants, as is obvious from combining (9b) or (10 b) with (2).

These phenomena give rise to fluorescent metamerism, in which samples which have identical apparent reflectance and apparent transmittance curves when measured with one rich illuminant can have non-identical apparent reflectance and apparent transmittance curves when measured with another rich illuminant.

It is important to note for the purposes of this invention that, although the apparent reflectance and apparent transmittance of a sample will vary with the illumination used in the measuring device, the apparent emissivity and apparent transmissivity are invariant. Similarly, although addition of a fluorescent colorant to a substrate will cause changes $\Delta R(\lambda)$ and $\Delta T(\lambda)$ in its apparent reflectance $R(\lambda)$ and transmittance $T(\lambda)$ which will vary with the illumination $S(\lambda)$ used in the measuring device, the changes $\Delta E(\lambda,\zeta)$ and $\Delta U(S\lambda,\xi)$ caused in its apparent emissivity $E(\lambda\xi)$ and transmissivity $U(\lambda,\xi)$ are invariant with illumination.

When there are plural absorption-emission relations between different bands, it is possible for fluorescent cascades to exist. In this case, the emission band of a first fluorescent relation is partly or wholly in the absorption band of a second fluorescent relation. Thus, part of the light emitted as a result of absorption in the first absorption band may be emitted in the second emission band, even when there is no incident light in the second absorption band. Such cascades can involve more than two fluorescent relations, and be complex in nature.

Methods whereby source metamerism and observer metamerism can be avoided in non-fluorescent materials are well-known. Most of these involve specifying, measuring, and controlling the reflectance spectrum of the material, rather than merely a set of colorimetric quantities. For example, U.S. Pat. No. 4,439,038 uses a least-squares approximation of the reflectance spectrum, while Shakespeare, J. and Shakespeare, T., "An Optimizing Color Controller", proc. TAPPI 1997 PCE&I at Birmingham Ala., 127–135, TAPPI Press, Atlanta USA, 1997 use a reflectance model to optimize colorimetric quantities in addition to the reflectance. U.S. Pat. No. 4,565,444 discloses methods whereby measurements of color are made across the entire width of a sheet without scanning by means of light pipes, or by providing illumination and detection across the entire sheet. U.S. Pat. No. 4,801,809 discloses a similar idea to U.S. Pat. No. 4,565,444, but implements it differently. U.S. Pat. No. 5,082,529 also discloses measurement and control of reflectance, adding Kubelka-Munk-type adjustments for infinite stack calculations.

In an attempt to quantify the effects of fluorescence, various modified spectrophotometers have been devised. In general, these employ additional rich light sources or optical filters to approximate each of plural specific illuminants, such as C, D65, F12 or intermittently removing some or all of the near ultraviolet from the approximation to an illuminant such as D65 or intermittently adding a rich ultraviolet illuminant to a specific illuminant such as C or D65.

Each of these techniques partly addresses the issue of measuring fluorescent metamerism, but none copes with it in a satisfactory way. Equally, none provides an adequate model for color control in the presence of fluorescent metamerism or for color control which will avoid or minimize the effects of fluorescent metamerism.

Removal of near-ultraviolet light from, and addition of near-ultraviolet light to an illuminant are equivalent in that they allow the apparent reflectance to be measured with different amounts of near-ultraviolet light in the illuminant. Thus, the sensitivity of apparent reflectance to near-ultraviolet light can be quantified. However, this technique completely fails to address fluorescence where both absorption and emission occur within the visible range. Similarly, it fails to address fluorescence where both absorption and emission occur within the near-ultraviolet range. Also, since rich near-ultraviolet sources are used, it does not distinguish between the different efficiencies in each quantum relation of a fluorescence from near-ultraviolet to visible. Thus, it cannot provide a model for addition or removal of near-ultraviolet light of different relative spectral distribution than that used in the measuring device. Another consequence is that it cannot provide a model for fluorescent cascades existing in any wavelength bands, whether near-ultraviolet or visible.

From colorimetric data alone, it is difficult or impossible to deduce the amounts of different colorants present in a sample, even when the nature of the substrate and colorants is known. However, if reflectance and/or transmittance spectral data are provided in the visible range of wavelengths, it becomes possible in some cases to estimate the amounts of known non-fluorescent colorants present, provided the spectral responses of all colorants are quantified and the reflectance and/or transmittance of the substrate is known. The estimation can be performed, for example, by modification of the control calculations disclosed in the above mentioned article "An Optimizing Color Controller", so that the difference in reflectance or transmittance between the substrate and the sample is optimally fitted by scaled combination of normalized spectral responses of the colorants, hence providing the amounts of colorants present as said scale factors. A different method is disclosed in U.S. Pat. No. 4,977,522 which omits consideration of the substrate, and hence applies only to opaque coatings such as paints. These estimation methods are unreliable if fluorescence is present to a significant degree either in the substrate or in the colorants even if the data covers the fluorescent absorption region as well as the fluorescent emission region, as a result of several of the issues discussed earlier.

The discussion thus far has concentrated mainly on the measurement of color and related issues, and colorimetry is concerned only with the range of wavelengths visible to humans. However, in relation to the properties of reflectance, transmittance, and fluorescence, and their effects, the issues raised are not limited to those wavelengths, but are valid over a much wider range.

Spectral reflectance and transmittance measurements both inside and outside the visible range are commonly used to determine the composition of samples. U.S. Pat. No. 5,250,811 discloses a method for analyzing the composition of a multilayer web by measuring spectral reflectance in the near infra-red region. This method employs polychromatic illumination, in a similar manner to the polychromatic illumination used in determining color by measurement of reflectance as discussed above, differing only in the wavelength range.

U.S. Pat. No. 5,155,546 discloses a method employing spectral reflectance measurements in the visible region for analyzing the composition of rock samples. Also, U.S. Pat. No. 4,602,160 discloses an apparatus for measuring diffuse spectral reflectance and spectral transmittance in the infra-red region, and for analyzing those measurements to estimate the content of specific substances in a material. In these latter two disclosures, the sample to be analyzed is illuminated with monochromatic or nearly monochromatic light at each of several wavelengths bands one at a time, but the measurement of the reflected or transmitted light does not employ a monochromator, although it may employ a filter to exclude wavelengths outside the range to be measured which is substantially the same as the whole gamut of illumination bands. Thus, the reflected or transmitted light measured when the sample is illuminated at wavelength $\zeta$ with a detector uniformly sensitive to wavelengths from $\lambda_{min}$ to $\lambda_{max}$ is given by:

$$reflected(\zeta) = \int_{\lambda min}^{\lambda max} E(\lambda, \zeta) S(\zeta) d\lambda \quad (101a)$$
$$= S(\zeta) \int_{\lambda min}^{\lambda max} E(\lambda, \zeta) d\lambda$$

$$transmitted(\zeta) = \int_{\lambda min}^{\lambda max} U(\lambda, \zeta) S(\zeta) d\lambda \quad (101b)$$
$$= S(\zeta) \int_{\lambda min}^{\lambda max} U(\lambda, \zeta) d\lambda$$

A simple modification of these equations is required if the detector is differently sensitive to different wavelengths between $\lambda_{min}$ and $\lambda_{max}$. For non-fluorescent samples, (101a) and (101b) give results substantially identical to (9a) and (9b), and for such samples, it is largely irrelevant whether the single monochromator is used in the illuminator or in the detector. The apparent reflectance and transmittance calculated using (1), (2) or (8) from measurements described by (101a) and (101b) are given by:

$$R(\zeta) = \int_{\lambda min}^{\lambda max} E(\lambda, \zeta) d\lambda \quad (102a)$$

$$T(\zeta) = \int_{\lambda min}^{\lambda max} U(\lambda, \zeta) d\lambda \quad (102b)$$

For non-fluorescent samples, the apparent reflectance measured in this way is clearly the true reflectance, $R(\zeta)=E(\zeta,\zeta)$, and the apparent transmittance is clearly the true transmittance, $T(\zeta)=U(\zeta,\zeta)$.

For fluorescent samples, the reflectance or transmittance calculated from measurements of this type does not exceed unity, but it fails to distinguish between luminescent and non-luminescent contributions to the measurement. This deficiency reduces the amount of information which can be used to determine composition or other properties of the sample from the spectral measurements, and a significant fluorescent emission leads to an error in the calculated reflectance or transmittance. This error leads to an overestimation of the reflectance or transmittance in the fluorescent absorption band rather than in the fluorescent emission band, as would happen in the case of a device employing a detector monochromator with a rich light source. This systematic problem obviously introduces further sources of error in estimating properties or composition of the measured material when fluorescent substances are present.

U.S. Pat. No. 3,904,876 discloses a method for determining the amount of ash in paper by measuring the absorption of one or more monochromatic X-ray beams. U.S. Pat. No. 4,845,730 discloses a method which combines infra-red absorption measurements at several wavelengths with an absorption measurement for a monochromatic X-ray beam and measurements of beta ray absorption in estimating the amounts of a base material and two or three other components present in a paper web. The measurements made according to these methods also are described by equations (101a) and (101b), except that a different essentially monochrome detector may be used for each monochrome illumination wavelength.

U.S. Pat. No. 5,778,041 discloses a method which employs two polychromatic X-ray beams whose spectral power distribution differ in a particular way, and by measuring the amount of each beam absorbed in passing through a paper web, estimate the amounts of specific substances in that web. A different detector may be employed for each beam, but, monochromators are not employed either on the illuminator or on the detectors. However, filters may be used in controlling the spectral power distributions of the two illuminator beams.

Prior art methods also exist for estimation of composition and other properties from reflectance and transmittance spectral measurements by reference to sets of calibration data measured on samples of known properties. These methods are used for reflectance, transmittance, and absorbance spectral measurements, obtained either with a monochromator on the illuminator or on the detector. U.S. Pat. No. 4,800,279 discloses a method using infra-red absorbance spectra of calibration samples of known physical properties to determine those infra-red wavelengths at which the absorbance correlates with a physical property to be quantified, and then estimate that property for a sample from its infra-red absorbance spectrum. U.S. Pat. No. 5,121,337 discloses a method for estimating unmeasured properties such as composition from spectral measurements on a sample, using a model fitted by least-squares fitting, principal components regression, or partial least-squares regression to spectral measurements and measurements of the desired property or composition for a set of calibration samples. U.S. Pat. No. 5,446,681 discloses a method which employs rule-based critera in addition to statistical procedures in the estimation of property or composition from spectral measurements on a sample and spectral measurements on a calibration set of known properties or composition.

The above methods for analyzing spectral measurements to estimate composition or other physical properties, and for use of calibration data sets in such methods have a number of common features: i) the spectral data or a simple variant thereof such as its derivative is fitted as a combination of particular component spectral factors which are suitably scaled, (ii) the particular component spectral factors or known combinations thereof are associated with the physical properties or composition variables, (iii) the physical properties or composition variables are calculated using coefficients in a specific relation from the fitting parameters of the associated component spectral factors, and (iv) the particular component spectral factors and coefficients for relations are either known a priori or are derived from calibration data. The reliability of this class of analysis method depends on the extent to which the requisite component spectral factors can be discerned in the measurement, and the extent to which those patterns are invariant both within the calibration data set and between the calibration data and the measurements to be analyzed. The presence of significant amounts of fluorescence, and especially variation in that fluorescence can severely comprise the accuracy and reliability of such analyses based on spectrophotometric or spectroscopic measurements.

SUMMARY OF THE INVENTION

The object of the present invention is to provide an improved method and apparatus for measuring color. Another object of the present invention is to provide an improved method and apparatus for measuring composition and other properties.

The method of the invention is characterized by comprising the steps of illuminating a sample of the material with at least three separate illumination bands singly or in combination, said illumination bands collectively substantially spanning at least the visible range, and measuring the light reflected or transmitted by the sample in each of the states of illumination with at least four light detector elements responsive to light in wavelength bands which collectively substantially span the visible range as an apparent emissivity or transmissivity.

The apparatus of the invention is characterized by comprising at least one arrangement producing at least three separate illumination bands which collectively substantially span at least the visible range, at least one arrangement containing at least four light detector elements responsive to light in wavelength bands which collectively span substantially all of the visible range, means for coordinating the operation of the arrangement producing the illumination bands and light detectors such that when a light source illuminates a sample the sample, the detectors measure the spectrum of the light reflected or transmitted from the sample as an apparent emissivity or transmissivity.

The basic idea of the invention is that the color of a material is measured by illuminating a sample of the material with at least three separate illumination bands singly or in combination, said illumination bands collectively substantially spanning the visible range and by measuring the light reflected or transmitted by the sample when it is illuminated with at least four light detector elements responsive to light in wavelength bands which substantially span the visible range. It is also beneficial that the width of the illumination bands differs in such a manner that the illumination bands are narrowest near the expected fluorescence absorption bands. According to a preferred embodiment, at least two separate illumination bands can be operated in such a manner that they illuminate the sample simultaneously.

An advantage of the invention is that the measurement of the color is independent of fluorescent metamerism as well as of source and field metamerism. Further the color of a material may be characterized under all conditions of illumination. The color of the material may be controlled during manufacture. The means of measuring color is independent of the conditions of the illumination and thus describes the color under any particular conditions of illumination. Further the color may be controlled such that fluorescent metamerism, source metamerism and field metamerism may be avoided or minimized or specific metameric effects may be achieved. The measurement is reasonably simple and can be performed within a reasonably short time.

A further advantage of the invention is that by measuring the emissivity or transmissivity of the sample, if the responses in apparent emissivity or transmissivity of the colorants are known, then the amounts of the known colorants present in the sample can be estimated in almost all cases. The estimation can be performed, for example, by a two-dimensional fitting by scaling normalized emissivity or transmissivity responses. If the data include the fluorescent absorption region and fluorescent emission region, then such estimation can include known fluorescent substances as well. Moreover, due to the potentially large amount of information in emissivity of transmissivity data, there in a degree of redundancy for measurement of fluorescent samples, so that it is possible to estimate the amounts of selected known colorants without necessarily knowing the nature of all colorants present. This can be accomplished for example by performing said fitting only in regions of the emissivity data where the responses of said selected known colorants have significant distinguishing features. Furthermore, this latter technique allows the amounts of known colorants to be estimated without necessarily knowing the emissivity or transmissivity of the substrate.

Yet another advantage of the invention is that by measuring the apparent emissivity or transmissivity of a material, it is possible to distinguish between fluorescent and non-fluorescent components of spectra, and to characterize the fluorescent relations precisely. Accordingly, the composition and other properties of a sample may be determined with greater accuracy from emissivity or transmissivity measurements than from traditional spectral measurements, especially when fluorescent substances are present. Each component of a material such as a paper web colors the web, either in the visible region or in the infra-red region, or in another range of wavelengths. According to a preferred embodiment, illumination and detection bands in the infra-red region are used to determine the infra-red emissivity or transmissivity of a material, and the composition of the material is estimated from said measurements.

A further advantage is that the measurement of emissivity and transmissivity allows a greater variety of signal processing techniques to be employed than is possible for prior art spectroscopic or spectrophotometric spectral measurements. Obviously, the spectrum measured using a single illumination condition can be subjected to similar techniques as those used in prior art. Equally, the spectrum of measurements at a single detector band made under each illumination condition may be subjected to similar techniques. Since plural such spectra are available for plural illumination conditions and for plural detector elements, more and different information is available compared to prior art measurements. Moreover, these signal processing techniques can be used on one or more apparent reflectance or transmittance or absorbance spectra calculated from the measured emissivity or transmissivity, providing the same information as would be available from said prior art measurements. However, it is also possible to employ image processing techniques or other two-dimensional signal processing methods directly on the emissivity and transmissivity. Any commonly known low-pass, high-pass, band-pass, smoothing, or noise suppression filtering may be used, and these may be either one-dimensional or two-dimensional. Also feature enhancement operations such as differentiation in one or both dimensions or convolution with a one- or two-dimensional transform may be used. The measurement of emissivity or transmissivity or a filtered or enhanced measurement may be transformed for feature extraction or other analysis by means of a one- or two-dimensional Fourier or Mellin or Wavelet or Wigner-Ville transformation, among others known to those skilled in the art of signal or image processing, as described for example in Poularikas, A. (ed.) "The Transforms and Applications Handbook", CRC Press, Boca Raton, Fla., 1996, or in Ifeachor, E., and Jervis, B. "Digital Signal Processing", Addison-Wesley, Wokingham UK, 1993, among others.

For the purposes of this specification, the term "self-luminous" includes the properties of non-fluorescent luminescence, so that an entity described as "non-self-luminous" is understood to be neither luminous nor non-fluorescently luminescent. A non-self-luminous entity may, however, be transparent, translucent, or opaque, be fluorescent or non-fluorescent, and be specular, glossy, or matte.

For the purposes of this specification, the term "visible" generally refers to the gamut of wavelengths to which the normal human retina is receptive. However, when considering the measurement of color of entities intended to be subject to instrumental optical telemetry, the term "visible" shall refer to the gamut of wavelengths to which such instruments are photosensitive, rather than to the aforesaid gamut of humanly-visible wavelengths. We thus contemplate use of the methods and apparatus invented herein in wavelength bands outside the visible band, and such use is within the scope of our invention. Also the term "color" refers not only to humanly-visible colors but also to colors sensed by an optical instrument. The limits for integration or summation in several of the cited equations would be modified as necessary to match the ranges of illumination and detection wavelengths used. Moreover, one or more quantities would be calculated from measurements which need not all be within the visible band, with observer functions for calculating scalar observations and suitable coefficients for calculating properties from said observations. The observer functions may be defined as sets of factors to be applied in linear or nonlinear relations with reflectance or transmittance spectra calculated at particular values or ranges of wavelengths for particular conditions of illumination, or in linear, affine, or nonlinear relations with emissivity or transmissivity for particular values or ranges of illumination and detection wavelengths. For example, an observation $P_1$ may be calculated using a linear observer function defined as set of factors $p_1$ in any of the following ways:

$$P_1 = \sum_j p_1(\lambda_j) R(\lambda_j) \quad (111a)$$

$$= \sum_j p_1(\lambda_j) \sum_k E(\lambda_j, \zeta_k) \frac{S_1(\zeta_k)}{S_1(\lambda_j)} \Delta \zeta_k$$

$$P_1 = \sum_j p_1(\lambda_j) T(\lambda_j) \quad (111b)$$

$$= \sum_j p_1(\lambda_j) \sum_k U(\lambda_j, \zeta_k) \frac{S_1(\zeta_k)}{S_1(\lambda_j)} \Delta \zeta_k$$

$$P_1 = \sum_k \sum_j p_1(\lambda_j, \zeta_k) E(\lambda_j, \zeta_k) \quad (111c)$$

$$P_1 = \sum_k \sum_j p_1(l_j, z_k) U(l_j, z_k) \quad (111d)$$

where in the case of (111a) and (111b), a particular illumination condition $S_1(\lambda)$ is specified for evaluation of observation $P_1$. Alternative definitions may employ the measurement of light absorbed (defined as the complement of reflectance or transmittance or emissivity or transmissivity) rather than the measurement of light detected. Additionally or alternatively, observers may be defined using filtered or enhanced or transformed versions of the emissivity or transmissivity measurements, or using linear or affine or nonlinear combinations of emissivity and transmissivity. An unmeasured property Q may then be estimated using one or more coefficients $q_1$ in a linear, affine, or nonlinear relation with one or more observations $P_i$, such as:

$$Q = q_l P_1 \quad (112a)$$

$$Q = q_0 + \sum_i q_i P_i \quad (112b)$$

$$Q = q_0 + q_l \log_e(P_1) \quad (112c)$$

$$Q = q_0 \prod_i P_i^{q_l} \quad (112d)$$

The CIE L*a*b* color space discussed earlier serves as an example of a nonlinear relation, in which the observations are the CIE tristimulus values calculated using the standard colorimetric observer functions.

Such observer functions and coefficients may be known a priori, or may be derived from measurements of emissivity or transmissivity or absorbance or reflectance or transmittance made on sets of calibration samples for which the properties to be estimated using observer functions are already known, or are measured by other means. Suitable observer functions and coefficients may be derived using chemometric methods such as partial-least-squares regression, as described in Höskuldsson, A., "PLS Regression Methods", Journal of Chemometrics, volume 2, pages 211–228, 1988, or using principal components regression or continuum regression or canonical correlation or other statistical techniques, as described for example in Basilevsky, A., "Statistical Factor Analysis and Related Methods", Wiley, New York, 1994, among others. For example, the proportions of certain constituents of the sheet may be thus inferred from infra-red measurements on the sheet using also a set of reference or calibration measurements. These reference calibration measurements comprise measurements of the emissivity or transmissivity at some or all combinations of illumination and detection wavelengths together with measurements of composition or other properties made by other means for each of several reference or calibration samples.

BRIEF DESCRIPTION OF THE INVENTION

Figure 2:
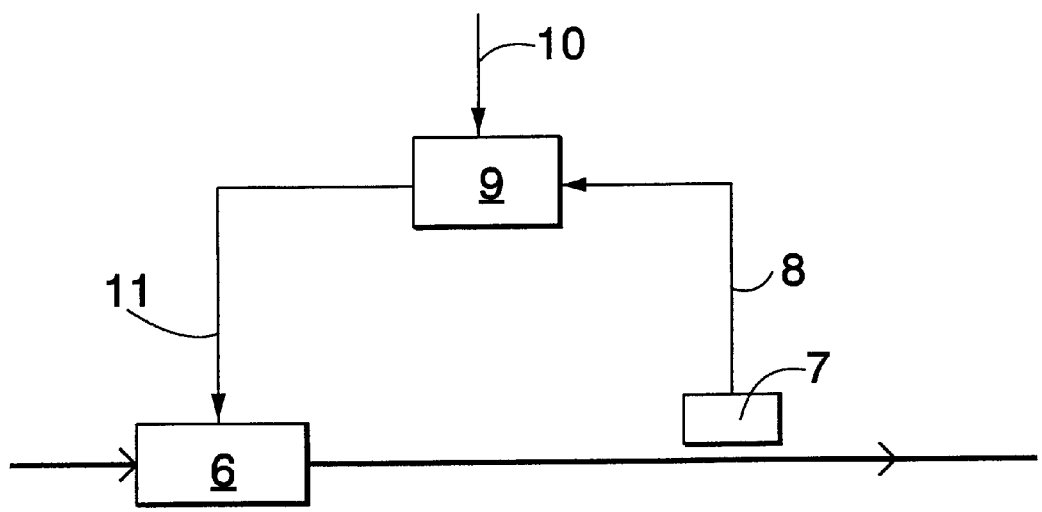

The invention will be described in greater detail in the accompanying drawing in which FIG. 1 is a schematic side view of a solution of the invention, and FIG. 2 illustrates schematically how a measurement of the invention is arranged to process control.

DETAILED DESCRIPTION OF THE INVENTION

FIG. 1 illustrates a web 1 the color and/or composition of which is measured. The web 1 is for example a paper web or a board web and is arranged to move in the direction of arrow A. An illuminator 2 is arranged to a measuring frame 4. The illuminator 2 comprises at least three light sources which emit light in wavelength bands which substantially span the visible range and preferably a range of shorter wavelengths. Thus the illuminator 2 produces light at the wavelength of several different illumination bands. Each illumination band illuminates the sheet 1 singly and in combination according to a predetermined sequence. A first detector 3a measures the light reflected by the sheet 1 when it is illuminated. The illumination bands may be noncontiguous, contiguous, or overlapping in wavelength. A second detector 3b measures the light transmitted by the sheet 1 when it is illuminated. Each detector 3a and 3b comprises at least four detector elements responsive to light in wavelength bands which substantially span the visible range. Preferably the detectors 3a and 3b have at least one additional light detector element responsive to light in shorter wavelength bands. The operation of the light sources and light detectors 3a and 3b is controlled with means 5 for coordinating such that when a light source illuminates the sample, the detectors measure the spectrum of the light reflected and/or transmitted from the sample. It is also possible to control the detectors to measure also when the sample is not illuminated to evaluate the effects of extraneous illumination.

The illuminator 2 is a source of light which can produce light of wavelengths within one or more substantially contiguous wavelength bands. The illuminator 2 may consist of a rich light source and a set of suitable optical filters or it may consist of plural distinct light sources each of which has suitable optical arrangements. The detectors 3a and 3b are sensitive to several wavelength bands independently.

Illumination of the sheet 1 can be made with individual illumination bands separately or with plural bands simultaneously. All wavelength bands in the detectors 3a and 3b simultaneously or independently for each state of illumination. The wavelength bands in the detector 3a need not correspond to those in the detector 3b, and wavelength bands in the detectors 3a and 3b need not correspond to illumination bands of the illuminator 2.

In a first embodiment of a light source arrangement, the wavelength bands for the light sources are substantially equal. In a second embodiment, wavelength bands which are not all equal are chosen for the light sources to provide measurements of the greatest utility using the fewest light sources. This choice will depend on the anticipated usage and its requirements so that light sources can be concentrated in the expected fluorescence absorption bands.

In an example of the second embodiment, when a near-white paper sheet is measured during manufacture, fluorescence occurs predominantly from near-ultraviolet to blue-visible wavelength bands. However, there may be more than one fluorescing constituent of the sheet, and each fluorescent constituent may differ from the others in its absorption and emission bands. Thus, in a simple case for measurement of color, one light source would span the near-ultraviolet from 300 nm to 400 nm, and another light source would span the visible range, from 400 nm to 700 nm. In this case, only two spectra need be measured to estimate the apparent emissivity or apparent transmissivity. A more sophisticated arrangement would employ a greater number of unequal bands for the light sources, such as 250–300 nm, 300–350 nm, 350–400 nm, 400–500 nm, and 500–800 nm. In this latter case, five spectral measurements would be required to estimate the emissivity or transmissivity, which estimates would be of correspondingly higher spectral resolution than in the former case. In other cases for measurement of composition, the light source arrangement may employ bands of various bandwidths in the infra-red or other wavelength regions. Source bands need not be contiguous in wavelength, and bands used in measuring composition and bands used in measuring color may exist in the same light source arrangement.

In an example of the first embodiment of an illumination band the range from 300 to 800 nm could be divided into illumination bands having a width of 20 nm, in which case the first illumination band $\lambda_1$ would be 300 to 320 nm, the second illumination band $\lambda_2$ 320 to 340 nm, the third illumination band $\lambda_3$ 340 to 360 nm etc., and the last illumination band $\lambda_{25}$ would be 780 to 800 nm. If the expected fluorescence absorption bands are between 300 and 400 nm, the illumination bands could be combined in such a manner that each illumination band $\lambda_1$ to $\lambda_5$ would illuminate the object independently and the sixth state in the illumination sequence would be a combination of illumination bands $\lambda_6$ to $\lambda_{15}$ which would illuminate in a wavelength band of 400 to 600 nm, and the seventh state would be a combination of illumination bands $\lambda_{16}$ to $\lambda_{25}$ which would illuminate in wavelength bands of 600 to 800 nm. In that case a sequence of only seven illumination states would be needed for achieving a very accurate result. If desired, illumination bands can be combined non-contiguously, and this can be accomplished without compromising the efficacy of measurement. For example, if fluorescent absorption at below 400 nm has emission which is entirely below 550 nm, then any or all illumination bands greater than 550 nm may be used simultaneously with any or each illumination band below 400 nm. This further reduces the number of illumination states required and speeds up the measurement process. An optimal illumination sequence can be chosen either from a priori knowledge of the fluorescent absorption and emission relations, or by measuring said relations with an illumination sequence in which each illumination band is used individually. The optimal sequence may also combine source bands for measuring color with source bands for measuring composition.

In a first embodiment of a light detector arrangement, the wavelength bands of the detector elements are of substantially equal width, which need not be the same as the width of any light source wavelength band. In a second embodiment, the wavelength bands of the detector elements substantially match the wavelength bands of the light sources in one of the light source arrangements. In a third embodiment, wavelength bands which are not all equal are chosen to provide measurements of the greatest utility using the fewest detector elements.

The invented method and apparatus measure the apparent emissivity and/or the apparent transmissivity of the sample, depending on the relative deployment of source arrangement and detector arrangement. Each row in the emissivity or transmissivity is measured as a single spectrum in the detector according to whether the detector is on the same side as or opposite the active light source. With reference to equations 11a and 11b, the wavelengths $\lambda_j$ are the central or average wavelengths of the detector elements, while the wavelengths $\zeta_k$ are the central or average wavelengths of the light sources.

Using measurements from a light detector arrangement opposite a light source arrangement, the apparent transmissivity is:

$$U_{jk} = \frac{transmit(j)}{incident(k)} \quad j = 1 \ldots N, \quad k = 1 \ldots M \tag{12a}$$

where incident light intensity is preferably measured at a time when there is no sample in the measurement position. Those skilled in the art will immediately recognize that 12a requires a detector which provides absolute measurements of light energy in each channel when $\lambda_j \neq \zeta_k$. Moreover, 12a requires an approximate correspondence between source wavelength bands and detector wavelength bands or groups of wavelength bands to provide the case $\lambda_j \neq \zeta_k$. However, it is possible to use a detector which provides only relative measurements of light energy in each channel, and which does not need to have spectral bands which match the source wavelength bands. In this latter case, measurements from different channels need not be directly comparable, and are derived by comparing them with the measurements made using one or more reference samples of known transmissivity. Apparent transmissivities $U_{jk}$, with $\lambda_j \neq \zeta_k$, are calculable where a reference sample has a known nonzero apparent transmissivity in the same band relation:

$$U_{jk} = \frac{transmit(j)}{transmit_{ref}(j)} U(\lambda_j, \zeta_k) \quad j = 1 \ldots N, \quad k = 1 \ldots M \quad (12b)$$

when illuminated by a light source of wavelength $\zeta_k$. If more than one reference sample has a nonzero apparent transmissivity in a particular band relation, then plural values based on the different references can be combined to estimate the apparent transmissivity. Apparent transmissivities $U_{jk}$, with $\lambda_j = \zeta_k$, are also calculable using 12b.

Similarly, using measurements from a light detector arrangement on the same side as a light source arrangement, the apparent emissivity is:

$$E_{jk} = \frac{reflect(j)}{incident(k)} \quad j = 1 \ldots N, \quad k = 1 \ldots M \quad (13a)$$

However, If there is no detector arrangement opposite the source arrangement, the incident light cannot be measured. Moreover, even if an opposite detector exists, its measurements may not be suitable for use in (13a), due to spectral resolution or calibration issues. In these cases, the apparent emissivity is calculated using measurements of reflected light from one or more references having known nonzero apparent emissivity values in the respective wavelength bands. Apparent emissivities $E_{jk}$, with $\lambda_j \neq \zeta_k$, are calculable where a reference sample has a known nonzero apparent emissivity in the same band relation:

$$E_{jk} = \frac{reflect(j)}{reflect_{ref}(j)} E_{ref}(\lambda_j, \zeta_k) \quad j = 1 \ldots N, \quad k = 1 \ldots M \quad (13b)$$

when illuminated by a light source of wavelength $\zeta_k$. If more than one reference sample has a nonzero apparent emissivity in a particular band relation, then plural values based on the different references can be combined to estimate the apparent emissivity. Apparent emissivities $E_{jk}$, with $\lambda_j = \zeta_k$, are also calculable using 13b.

Equations 12a, 12b, 13a, 13b assume that the wavelength bands can be completely separated in the measurements of reflected and transmitted light. In practice, such ideal band separation is impossible, and optical components such as monochromators and polychromators with better band separation characteristics are more costly. However, if the band overlap characteristics of the components used in the instrument are approximately known, the measured light spectra can be deconvoluted. This method provides improved estimates of the spectra which would be obtained if the optical components were ideal. For example, if the band overlap matrices are known for the source bands and for the detector bands, then the apparent emissivity matrix can be deconvoluted:

$$E_{corr} = (B_{reflect} B_{source})^{-1} E_{meas} \quad (14a)$$

where $E_{meas}$ is the measured emissivity matrix, $E_{corr}$ is the deconvoluted emissivity, $B_{source}$ is the source band interaction matrix, and $B_{reflect}$ is the band interaction matrix for the reflected light detector. The apparent transmissivity matrix may similarly be deconvoluted:

$$U_{corr} = (B_{transmit} B_{source})^{-1} U_{mea} \quad (14b)$$

where $U_{meas}$ is the measured transmissivity matrix, $U_{corr}$ is the deconvoluted transmissivity, and $B_{transmit}$ is the band interaction matrix for the transmitted light detector. Deconvolution may alternatively be performed on apparent reflectance and apparent transmittance spectra derived from undeconvoluted emissivity and transmissivity matrices.

The apparent emissivity and apparent transmissivity of a sample do not depend on the source used to illuminate the sample. Rather, they describe how the sample's appearance will change as the illuminant is varied. Thus, specification of the apparent emissivity and/or apparent transmissivity is a better characterization of color than mere specification of reflectance and/or transmittance under one or more particular conditions.

Apparent reflectances and apparent transmittances for arbitrary known illuminants may be calculated from the apparent emissivity and apparent transmissivity, respectively. This calculation can employ (10a) or (10b), for example, in combination with (8) or (2). Also, colorimetric quantities and related non-colorimetric quantities can clearly be calculated from such apparent reflectances and apparent transmittances. Such calculations of apparent reflectance, apparent transmittance, and associated colorimetric and non-colorimetric quantities can clearly be performed for plural known illuminants. Similarly, the light measured by illuminating with monochrome or narrow-band illuminators while measuring with a single detector of known broad bandwidth can be calculated. This calculation can employ (101a) or (101b) for example. The apparent reflectance or apparent transmittance spectrum which would be measured by such a method can also be calculated, for example using (102a) or (102b), whence the apparent absorption can be calculated using (3).

Since an apparent reflectance and transmittance may be calculated for arbitrary illuminants from the apparent emissivity and apparent transmissivity, it is possible to calculate the light which would be reflected or transmitted if the sample were measured using a spectrophotometer or spectroscope of known source characteristics. If the monochromator and detector characteristics of that spectrophotometer or spectroscope are also known, especially its band interaction matrix, it is then possible to calculate the reflectance or transmittance or absorbance which it would measure.

By measuring the change in apparent emissivity and/or the change in apparent transmissivity of a sheet during manufacture, when the process conditions are changed, the effect of such process changes can be characterized in terms of effects on apparent emissivity and/or apparent transmissivity. Such characterization can further be parametrized in terms of values for a number of parameters and the values of process variables and the change effected on process conditions. Said parametrization can be purely phenomenological, or can include a mathematical model for the process. Thus, the expected change in emissivity and/or the expected change in transmissivity which would result from a change in process conditions can be subsequently computed from said parameters for different values of said process variables.

From such a characterization, the effects of said process changes can be calculated for arbitrary known illuminants in terms of an effect on the apparent reflectance and/or apparent transmittance under such conditions of illumination.

Furthermore, from such a characterization, the effects of said process changes can be calculated for arbitrary known illuminants in terms of an effect on colorimetric quantities or related non-colorimetric quantities under such conditions of illumination. Similarly, from such a characterization, the effects of said process changes can be calculated in terms of an effect on one or more composition quantities or other properties which can be estimated from the emissivity or transmissivity measurement.

For example, if the expected change in emissivity resulting from a change in process conditions is ΔE and the expected change in transmissivity is ΔU, then the expected changes in reflected light and in transmitted light which would be measured using an illuminant S can be calculated:

$$\Delta reflected(\lambda) = \int_{min}^{780} \Delta E(\lambda, \zeta) S(\zeta) d\zeta \quad (15a)$$

$$\Delta transmitted(\lambda) = \int_{min}^{780} \Delta U(\lambda, \zeta) S(\zeta) d\zeta \quad (15b)$$

A matrix representation of these equations is also possible. The ability to compute the change under arbitrary illuminants, including under each of plural illuminants is particularly valuable in color control, especially when multiple color targets are given for each of plural illuminants.

By measuring color in a way which is independent of the illumination, it becomes possible to regulate the color of a material independently of the illumination. In this way, the color of the material may be regulated for all illuminants, by using a target which is independent of illumination. Alternatively, since reflectances and transmittances can be evaluated for each of plural illuminants, specific reflectance or transmittance color targets can be provided for each of plural conditions of illumination, and the color of the material may be regulated to provide the closest match to those targets. Alternatively, colorimetric targets may be provided for plural specific illuminants, and the color of the material regulated to provide the closest match to those targets. In a similar way, the process may be governed to regulate the values of one or more composition quantities which can be estimated from emissivity or transmissivity measurements.

In practice, regulating the color measurement to achieve an exact match with the color target using the available means of modulating the process may not always be possible, or may be expensive,. This situation can occur even if only a single colorimetric target is supplied for a single illuminant. It is more common when multiple colorimetric and/or spectral targets are supplied for different illuminants, or when an illuminant-independent target is supplied. In these cases, a control algorithm which minimizes the difference between the color measurement and the color target, optionally using weighting factors on each component of the target, can provide the nearest match over the set of targets. The difference function to be minimized can also include the costs and usage of materials and other resources which are used by the means of modulating the coloring process, as well as limits on their allowed usage, in calculating an optimal control action.

FIG. 2 illustrates how the measurement of the invention is arranged to control process 6. The process 6 may be for example a paper or cardboard or paperboard or tissue manufacturing process producing the web 1. The color or composition of the web 1 is measured with a measuring arrangement 7. A color or composition measurement 8 yielded by the measurement arrangement 7 is led into a controller 9. A color or composition target 10 is also fed into the controller 9. On the basis of the color or composition measurement 8 and color or composition target 10 the controller 9 controls the process 6 by means of a control signal 11.

The controller 9 calculates a change for at least one manipulable process variable so as to reduce the difference between the color or composition measurement 8 and the color or composition target 10 and governs said manipulable process variables to accomplish the calculated change. The manipulated process variable may be a condition of processing of the material, especially conditions taken from the list: temperature; pressure; irradiation; mechanical agitation or electric potential. Further, the manipulated process variable may be a chemical condition to which the material or of one or more of its constituents is exposed, especially conditions taken from the list: pH; presence and concentration of cations or anions; presence and concentration of chemical activators or inhibitors or other agents for inducing or suppressing reactions; presence and concentration of catalysts, or other agents for facilitating reactions. For control of color, the manipulated variable may further be the combinatory proportion of a colorant in the material, especially colorants taken from the list: dyes; bleaches; brighteners; whiteners; fluorescence inhibitors; tinting agents; opacity agents; pigments, fluorescent colorants; fluorescent brighteners; fluorescent pigments; pre-colored feedstocks or feedstocks of different colors. For control of composition, the manipulated variable may further be the combinatory proportion of a feedstuff in the material, especially feedstuffs taken from the list: filters; sizing; coatants; recycled stocks or stocks of different constituent substances; or may be the concentration of a substance in a feedstuff.

The color target 10 may be specified in at least one of the following ways: as desired values of emissivity; as desired values of transmissivity; as desired values of one or more apparent reflectance spectra with particular conditions of illumination; as desired values of one or more apparent transmittance spectra with particular conditions of illumination or as desired values of one or more sets of colorimetric quantities with particular conditions of illumination and observation. The controller 9 may comprise means for supplying weighting factors for the color target 10 specified in at least one of the following ways corresponding to one or more of the ways the color target is supplied: as weighting factors for emissivity values; as weighting factors for transmissivity values; as weighting factors for one or more reflectance spectra; as weighting factors for one or more transmittance spectra or as weighting factors for one or more sets of colorimetric quantities. Said weighting factors are used in calculating the difference between the color measurement 8 and the color target 10. The controller 9 may further comprise means for supplying quality acceptance ranges for the color target specified in at least one of the following ways, corresponding to one or more of the ways the color target 10 is supplied: as a range of acceptable emissivty values; as a range of acceptable transmissivity values; as one or more ranges of acceptable reflectance spectra; as one or more ranges of acceptable transmittance spectra or as one or more ranges of acceptable colorimetric quantities. Said ranges are used in calculating the difference between the color measurement 8 and the color target 10.

Composition and other targets 10 may be specified according to the manner of estimation of their measurements 8. For example, composition targets 10 may be specified as percentual or fraction content of a component in the material by mass or volume, or as an amount or mass of a component per unit area of the material. Targets 10 may also be supplied for one or more of the scalar observation quantities from which composition or color or other properties are estimated. The controller 9 may comprise weighting factors for these composition and other targets, and may further comprise means for supplying quality acceptance ranges for one or more such targets.

In one embodiment of the invention the color or composition of a sample of the material is measured when the process 6 is in a first substantially steady state. Thereafter, a change is induced in a manipulable process variable causing the process to reach a second substantially steady state. The color or composition of a sample of the material is measured when the process is in the second substantially steady state. The difference between the color or composition measurements in the first and second steady states is scaled according to the size of the change induced in the manipulated variable to produce a normalized color or composition change and the effect of the manipulated variable is characterized in terms of the normalized color or composition change. The timing of changes in the color or composition of the material as the process moves from the first to the second steady state may be observed and the effect of the manipulated variable may be characterized in terms of the normalized color or composition change and its timing parameters.

The drawing and the related description are only intended to illustrate the inventive concept. The details of the invention may vary within the scope of the claims. Therefore the possible combinations of this invention with prior art are many and varied. For example, the measurement of color or composition profile may be combined with art for separation of MD- and CD-components of variability, such as by deploying measurement devices at each of plural locations across the web, or by employing light pipes from a measurement device to convey light to and from each of plural locations across the web. The directional illumination or directional light detection may be combined with art for illumination or detection in an annulus or in one or more arcs. The characterization of the effect of process changes may be combined with prior art for process model identifications. The measurement of reflected light may be combined with prior art for alternating sample backings of different reflectance. The control of color or composition may be combined with prior art for optimal control, especially using methods for constrained optimization. Furthermore, the control of color or composition according to this invention may be combined with art for control of properties in the cross-machine direction, such as disclosed in WO 98/32916. Similarly, the set of calibration samples shown in FIG. 1 with broken lines used in determining the factors and coefficients for estimating properties from the emissivity and/or transmissivity measurements or from a calculated apparent reflectance and/or transmittance and/or absorbance may be provided within the apparatus for regular recalibration, or may be furnished externally from time to time for intermittent recalibration. Additionally or alternatively, calibration samples may be measured using other means, and those measurements or factors and coefficients determined therefrom may be supplied to the means for determining properties from the emissivity or transmissivity measurements. The samples may be chosen with properties which facilitate the calibration process, for example by optimizing the amount of information which can be deduced by the statistical method used in determining the factors and coefficients. Suitable techniques are given for example in Box, G., and Draper, N., "Empirical Model-Building and Response Surfaces", Wiley, New York, 1987, among others. Moreover, similar techniques can be applied to characterizing the effect of manipulating process variables on measured properties, in that optimally selected sets of process disturbances can be used which facilitate the identification and parametrization of said process effects.

Moreover, as the art of color measurement and control advances, common conventions and recommendations may be revised by the generally accepted standards authorities in the art. For example, new instrument geometries or colorimetric formulae may be adopted in a future standard. This invention anticipates such revisions, and should be understood to cover such, where extension of this specification to provide such coverage would require mere substitution of the new term in place of an existing like term, or would require merely adding the new term to a list of existing like terms.

In an embodiment for measurement of reflected light, a light detector arrangement is located on the same side of the sample as the light source arrangement. In an embodiment for measurement of transmitted light, a light detector element is located on the opposite side of the sample to the light source arrangement. In one embodiment for measurement of both reflected and transmitted light, a light source arrangement is located on one side of the sample, and light detector arrangements are located on both sides of the sample. In another embodiment for measurement of both reflected and transmitted light, light source arrangements are located on both sides of the sample, and a light detector arrangement is located on one side of the sample. In yet another embodiment for measurement of both reflected and transmitted light, light source arrangements are located on both sides of the sample, and light detectors are located on both sides of the sample.

In an embodiment for measuring color or composition of a moving sheet, the apparatus comprising one or more light source arrangements and one or more light detection arrangements is deployed in a scanning apparatus which traverses the sheet in a direction substantially perpendicular to the direction of movement of the sheet. In another embodiment, plural apparatuses each comprising one or more light source arrangements and one or more light detection arrangements are employed in plural locations in a non-scanning apparatus which is positioned across the path of the moving sheet. In a variation on this embodiment, the apparatus may scan over the moving sheet with a scan distance which is substantially equal to the separation between the light paths of the plural arrangements, so that substantially the whole width of the sheet is measured. In a further embodiment, light pipes are used to convey light from one or more light source arrangements to each of plural locations across the sheet, and light pipes are used to convey light reflected from or transmitted through the sheet at each of plural locations across the sheet to one or more light detector arrangements, where said source arrangements and detector arrangements need not be equal in number and need not be situated across the path of the moving sheet.

In the above mentioned embodiments, a light source arrangement may be constructed so that the sample is illuminated in any practical geometrical relation to the sample. Preferably, the sample is illuminated substantially according to one of the following geometries: perpendicularly to the sample (0 geometry); from one or more directions, each subtending an angle of approximately 8 degrees from the perpendicular (8 geometry); from one or more arcs, each subtending an angle of approximately 8 degrees from the perpendicular (8 geometry); from an annulus subtending an angle of approximately 8 degrees from the perpendicular (8 geometry); from one or more directions, each subtending an angle of approximately 45 degrees from the perpendicular (45 geometry); from one or more arcs, each subtending an angle of approximately 45 degrees from the perpendicular (45 geometry); from an annulus subtending an angle of approximately 45 degrees from the perpendicular (45 geometry) or diffusely, with incident light substantially at all angles (d geometry).

In the above mentioned embodiments, a light detector arrangement may be constructed so that the transmitted or reflected light is detected in any practical geometrical relation to the sample. Preferably, the light is detected substantially according to one of the following geometries: perpendicularly to the sample (0 geometry); from one or more directions, each subtending an angle of approximately 8 degrees from the perpendicular (8 geometry); from one or more arcs, each subtending an angle of approximately 8 degrees from the perpendicular (8 geometry); from an annulus subtending an angle of approximately 8 degrees from the perpendicular (8 geometry); from one or more directions, each subtending an angle of approximately 45 degrees from the perpendicular (45 geometry); from one or more arcs, each subtending an angle of approximately 45 degrees from the perpendicular (45 geometry); from an annulus subtending an angle of approximately 45 degrees from the perpendicular (45 geometry); diffusely, with detected light at substantially all angles (d geometry) or diffusely, with detected light substantially at all angles, except the angle of directional illumination (t geometry). The various geometrical embodiments may be combined, so that either illumination or detection or both may be performed in plural geometries with respect to the sample, simultaneously, individually or independently.

What is claimed is:

1. In a method for determining the color and/or composition of a material, the improvements comprising the steps of:
   illuminating a sample of the material with at least three separate illumination bands singly or in combination, said illumination bands collectively substantially spanning at least the visible range; and
   measuring the light reflected or transmitted by the sample in each of the states of illumination with at least four light detector elements responsive to light in wavelength bands which collectively substantially span at least the visible range as an apparent emissivity or transmissivity.

2. A method according to claim 1, wherein the width of the illumination bands differ in such a manner that the illumination bands are narrowest near the expected fluorescence absorption bands.

3. A method according to claim 1, wherein at least two separate illumination bands are combined in such a manner that they illuminate the sample simultaneously.

4. A method according to claim 1, wherein at least one illumination band spans a range of wavelengths shorter than the visible ones.

5. A method according to claim 1, wherein at least one light detector element is responsive to light at wavelengths shorter than the visible ones.

6. A method according to claim 1, the method further comprising the steps of
   evaluating at least one scalar observation quantity by applying factors in a first specified relation to the elements of said emissivity or transmissivity or the elements of a part thereof, and
   estimating a property of the measured material from at least one scalar observation quantity by applying at least one coefficient in a second specified relation to said scalar observations(s).

7. A method according to claim 6, wherein the first and second specified relations are weighted summations, such that
   the elements are multiplied by the factors and then summed to yield the scalar observation, and
   the observations are multiplied by the coefficients and then summed to yield the estimate of the property.

8. A method according to claim 6, wherein the first specified relation employs a nonlinear operation.

9. A method according to claim 6, wherein the second specified relation employs a nonlinear operation.

10. A method according to claim 6, wherein said factors and coefficients are determined using a set of calibration samples whereof the properties to be estimated are known and using a method of statistical analysis applied to said known properties and to measurements of emissivity and/or transmissivity of said calibration samples.

11. A method according to claim 10, wherein said method of statistical analysis is taken from the list: linear least-squares regression; nonlinear least-squares regression; partial least-squares regression; principal components regression; quadratic principal components regression; continuum regression; ridge regression; latent root regression; factor analysis regression; canonical correlation.

12. A method according to claim 6, wherein the first specified relation comprises calculating a transformation of said emissivity or transmissivity or of a part thereof, applying said factors in a linear or nonlinear relation thereto, and combining the results linearly or nonlinearly into a scalar observation quantity, and especially wherein said transformation is differentiation or integration in one or both dimensions or is a Fourier or Mellin or Wavelet or Wigner-Ville transformation in one or two dimensions, or is an autocorrelation in one or two dimensions or a cross-correlation between rows or columns of the measurement or a convolution with a specified one or two dimensional function, or is a low-pass, band-pass, band-stop, or high-pass filter in one or two dimensions.

13. A method according to claim 1, wherein the calculation of emissivity or transmissivity incorporates a deconvolution operation to compensate for non-ideality of the optical components.

14. A method according to claim 1, the method further comprising the step of calculating the apparent reflectance or transmittance or absorbance of the sample corresponding to at least one known illuminant using the aforesaid measurement.

15. A method according to claim 14, the method further comprising the steps of
   evaluating at least one scalar observation quantity by applying factors in a first specified relation to the elements of said apparent reflectance or transmittance or absorbance or to the elements of a part thereof, and
   estimating a property of the measured material from at least one scalar observation quantity by applying at least one coefficient in a second specified relation to said scalar observations(s).

16. A method according to claim 15, wherein the first and second specified relations are weighted summations, such that
   the elements are multiplied by the factors and then summed to yield the scalar observation, and the observations are multiplied by the coefficients and then summed to yield the estimate of the property.

17. A method according to claim 15, wherein the first specified relation employs a nonlinear operation.

18. A method according to claim 15, wherein the second specified relation employs a nonlinear operation.

19. A method according to claim 15, wherein said factors and coefficients are determined using a set of calibration samples whereof the properties to be estimated are known and using a method of statistical analysis applied to said known properties and to measurements of apparent reflectance and/or transmittance and/or absorbance of said calibration samples.

20. A method according to claim 19, wherein said method of statistical analysis is taken from the list: linear least-squares regression, nonlinear least-squares regression; partial least-squares regression; principal components regression; quadratic principal components regression; continuum regression; ridge regression; latent root regression; factor analysis regression; canonical correlation.

21. A method according to claim 14, wherein the first specified relation comprises calculating a transformation of the apparent reflectance or transmittance or absorbance spectrum or of a part thereof, applying said factors in a linear or nonlinear relation thereto, and combining the results linearly or nonlinearly into a scalar observation quantity, and especially wherein said transformation is differentiation or integration or is a Fourier or Mellin or Wavelet or Wigner-Ville transformation, or is an autocorrelation or a convolution with a specified function, or is a low-pass, band-pass, band-stop, or high-pass filter.

22. A method according to claim 14, the method further comprising the step of calculating indices of metamerism for at least one pair of such calculated apparent reflectances or transmittances, especially for the quantities taken from the list:

fluorescent index; fluorescent metamerism index; field metamerism index; source metamerism index; illuminant metamerism.

23. A method according to claim 1, the method further comprising the steps of measuring the color and/or composition of a sample of the material using the aforementioned measurement when the process is in a first substantially steady state;

inducing a change in a manipulable process variable causing the process to reach a second substantially steady state;

measuring the color and/or composition of a sample of the material using the aforementioned measurement when the process is in the second substantially steady state;

scaling the difference between the said measurements in the first and second steady states according to the size of the change induced in the manipulated variable to produce a normalized change and characterizing the effect of the manipulated variable in terms of the normalized said change.

24. A method according to claim 1, the method further comprising the steps of comparing the measurement of quantities derived therefrom to a color and/or composition target;

calculating a change for at least one manipulable process variable so as to reduce the difference between the said measurement and the said target; and governing means of modulating said manipulable process variables to accomplish the calculated change.

25. A method according to claim 24, wherein weighting factors are employed in the determination of the difference between said measurement and said target.

26. A method for determining the composition of a material according to claim 1, wherein the visible range is a range of wavelengths which are instrumentally detectable, and especially a range of wavelengths in the x-ray, ultraviolet, infra-red, or microwave bands.

27. A method according to claim 1, wherein the material the color or composition of which is determined is paper or cardboard or paperboard or tissue.

28. In an apparatus for determining the color and/or composition of a material, the improvements comprising:

at least one arrangement producing at least three separate illumination bands which collectively substantially span at least the visible range, at least one arrangement containing at least four light detector elements responsive to light in wavelength bands which collectively substantially span at least the visible range, and means for coordinating the operation of the arrangement producing the illumination bands and containing the light detectors such that when a light source illuminates a sample of the material, the detectors measure the light reflected or transmitted by the sample as an apparent emissivity or transmissivity.

29. A method according to claim 28, wherein the width of the illumination bands differs in such a manner that the illumination bands are narrowest near the expected fluorescence absorption bands.

30. An apparatus according to claim 28, the apparatus further comprising means for coordinating the illumination bands to illuminate the sample singly and in combination according to a predetermined sequence.

31. An apparatus according to claim 28, the apparatus further comprising means for combining at least two separate illumination bands in such a manner that they illuminate the sample simultaneously.

32. An apparatus according to claim 28, wherein at least one illumination band spans a range of wavelengths shorter than the visible ones.

33. An apparatus according to claim 32, wherein at least one light detector element is responsive to light at wavelengths shorter than the visible ones.

34. An apparatus according to claim 28, the apparatus further comprising means for determining a composition property of the measured material from the measurements of emissivity or transmissivity.

35. An apparatus according to claim 34, the apparatus further comprising at least one calibration sample which can be moved into a position in which its emissivity and/or transmissivity can be measured, and whereof the properties to be determined are known.

36. An apparatus according to claim 34, the apparatus further comprising means for calculating from measurements of at least one calibration sample suitable factors and coefficients to be used in a relation for estimating the properties to be determined.

37. An apparatus according to claim 28, the apparatus further comprising means for comparing the measurement or quantities derived therefrom to a target, means for calculating a change for at least one manipulable process variable so as to reduce the difference between the said measurement and the said target and means for governing means of modulating said manipulable process variables to accomplish the calculated change.

38. An apparatus according to claim 37, the apparatus further comprising means for applying weighting factors in the determination of the difference between said measurement and said target.

39. An apparatus according to claim 28, wherein the material the color or composition of which is determined is paper or cardboard or paperboard or tissue.

* * * * *